United States Patent
Moon (10) Patent No.: US 11,480,576 B2
(45) Date of Patent: Oct. 25, 2022

(54) CONJUGATED OLIGOMER-BASED MACROCYCLES FOR LIVE CELL IMAGING

(71) Applicant: Joong Ho Moon, Weston, FL (US)

(72) Inventor: Joong Ho Moon, Weston, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 785 days.

(21) Appl. No.: 16/433,243

(22) Filed: Jun. 6, 2019

(65) Prior Publication Data

US 2020/0386763 A1 Dec. 10, 2020

(51) Int. Cl.
| | |
|---|---|
| *C07D 273/00* | (2006.01) |
| *G01N 33/58* | (2006.01) |
| *G01N 21/64* | (2006.01) |
| *C08G 18/18* | (2006.01) |

(52) U.S. Cl.
CPC ......... *G01N 33/582* (2013.01); *C07D 273/00* (2013.01); *C08G 18/1808* (2013.01); *G01N 21/6428* (2013.01); *G01N 21/6456* (2013.01); *G01N 2021/6439* (2013.01)

(58) Field of Classification Search
CPC .................................................. C07D 273/00
See application file for complete search history.

(56) References Cited

PUBLICATIONS

Iyoda, M., et al., "Conjugated Macrocycles: Concepts and Applications." Angewandte Chemie International Edition, 2011, 50(45): 10522-10553.
Osaki, H., et al., "A Macrocyclic Fluorophore Dimer with Flexible Linkers: Bright Excimer Emission with a Long Fluorescence Lifetime" Angewandte Chemie , 2016, 128(25): 7247-7251.
Shirinfar, B., et al., "Charged probes: turn-on selective fluorescence for RNA." Organic & Biomolecular Chemistry, 2018, 16(2): 164-168.
Wadhavane, P.D., et al., "Fluorescent macrocyclic probes with pendant functional groups as markers of acidic organelles within live cells." Organic & Biomolecular Chemistry, 2014,12(5): 823-831.
Wang, B., et al., "Precisely Defined Conjugated Oligoelectrolytes for Biosensing and Therapeutics." Advanced Materials, 2019, 31(22): 1806701, pp. 1-21.

*Primary Examiner* — Bruck Kifle
(74) *Attorney, Agent, or Firm* — Saliwanchik, Lloyd & Eisenschenk (57) ABSTRACT

A phenyleneethynylene macrocycle (PEMC) is constructed that is a cyclic or polycyclic oligo (oligophenyleneethynylene-co-polyamine) where a monodispersed oligophenyleneethynylene is coupled with a polyamine. The PEMC is formed by coupling a monodispersed di-aldehyde end-capped oligophenyleneethynylene with a polyamine to form a macrocyclic imine and reducing the imine to an amine. The PEMC is useful at entering living cells for the fluorescence imaging of the living cells without toxicity to the cells.

20 Claims, 8 Drawing Sheets

CONJUGATED OLIGOMER-BASED MACROCYCLES FOR LIVE CELL IMAGING

This invention was made with government support under DMR 1352317 awarded by the National Science Foundation. The government has certain rights in the invention.

BACKGROUND OF INVENTION

Fluorescent labelling of intracellular organelles, proteins, or nucleic acids (NAs) is an essential way of studying the structure and function of live cells. Conjugated polymers (CPs) and conjugated polymer nanoparticles (CPNs) have been shown to be useful for labelling, sensing, and delivery of biological substances owing to their excellent photophysical (i.e., high molar absorptivity, quantum yield, and photostability) and biophysical (i.e., nontoxicity and biocompatibility) properties. However, relatively large molecular weights and broad molecular weight distributions of CP-based materials often limit their intracellular applications in live cells. To address the limitation associated with the size of CPs, introducing disulfide-containing CPNs allows highly specific mitochondria labelling via efficient cellular entry followed by intracellular degradation to low molecular weight oligomers. (See U.S. Pat. No. 9,757,410)

Molecularly defined short conjugated oligomers (COs) are better suited for intracellular labelling than CPs or CPNs. Quantum yields (QYs) of short phenyleneethynylene (PE)-based oligomers, are generally higher than those of the equivalent CPs because QYs decrease as the conjugation lengths increase due to the decreased contribution of vibrational deactivation. COs with appropriate functional groups are highly water-soluble, making applications in aqueous environments ideal. Low molecular weight amphiphilic COs, generally trimers through pentamers, due to a smaller hydrodynamic volume, appear to enter cells by fast diffusion through the cell membranes, whereas CPs and CPNs are most likely endocytosed and entrapped in endosomes or lysosomes. Despite their advantages, there are few examples of COs being used for fluorescent labelling applications in live cells. COs must be modified with functional groups as side chain or chain-ends to achieve targeting or sensing functions. It is desirable to retain the advantageous of a high absorbance of the CPs with the high QYs and high rate of cellular entry of the COs.

BRIEF SUMMARY

And embodiment of the invention is directed to a phenyleneethynylene macrocycle (PEMC), where the PEMC is a cyclic or polycyclic oligo (oligophenyleneethynylene-co-polyamine) where the polyamine is a diamine, triamine or tetraamine coupled with the oligophenyleneethynylene is a monodispersed dimer, trimer, tetramer, or pentamer. The oligophenyleneethynylene is of the structure:

where n is 0 to 4 and R is independently H, $C_1$-$C_3$ alkyl, or $C_1$-$C_3$ alkoxy where any of the carbons may be unsubstituted or substituted with: an amine or protected amine comprising substituent; a OH or protected hydroxy comprising substituent; a SH or protected thiol comprising substituent; an amide comprising substituent; or a guanidine or protected guanidine comprising substituent; where the substituent optionally comprises: an $C_2$-$C_5$ alkylene oxide dimer, trimer, tetramer, or pentamer; an unprotected or protected $C_2$-$C_5$ alkylene imine dimer, trimer, tetramer, or pentamer; or N-substituted $C_1$-$C_3$ alkyl alkylene imine dimer, trimer, tetramer, or pentamer. The polyamine can be a diamine of the structure:

where X is: $(CR_2)_x$ where x is 1-3 and Rs are independently H, $C_1$-$C_6$ alkyl, or phenyl; $(CR_2)_y C_6 H_z R_{4-z} (CR_2)_y$, where y is 0-2, z is 0-4, and R is independently H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4 and where X is optionally interrupted one or more times with a disulphide, ester, acetal, or ketal. The polyamine can be the triamine of the structure:

where Y is: $((CR_2)_x)_3 CR$ where x is independently 0-3 and Rs are independently H, $C_1$-$C_6$ alkyl, or phenyl; $((CR_2)_y)_3 C_6 H_z R_{3-z}$ where y is 0-2, z is 0-3, and R is H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4 and where Y is optionally interrupted one or more times with a disulphide, ester, acetal, or ketal. The polyamine can be a tetraamine of the structure:

where Z is: $((CR_2)_x)_4 C$ where x is independently 0-3 and Rs are independently H, $C_1$-$C_6$ alkyl, or phenyl; $((CR_2)_y)_4 C_6 H_z R_{2-z}$ where y is 0-2, z is 0-2, and R is H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4 and where Z is optionally interrupted one or more times with a disulphide, ester, acetal, or ketal. The cyclic oligo (oligophenyleneethynylene-co-polyamine) can be a unimacrocycle (2/1). The polycyclic oligo (oligophenyleneethynylene-co-polyamine) can be a trimacrocycle (3/3); a tetramacrocycle (3/6); a tetramacrocycle (4/4); or a hexamacrocycle (4/6). The PEMC can have the amines of the cyclic oligo (oligophenyleneethynylene-co-polyamine) in the form of an ammonium ion paired with a anion from the acid used for protonation, where the acid is acetic acid, trifluoroacetic acid or a hydrogen halide, such as HCl, HBr, or HI.

In an embodiment of the invention, the PEMC is prepared by combining a monodispersed di-aldehyde end-capped oligophenyleneethynylene with a polyamine to form a macrocyclic imine, followed by reduction of the imine to an amine. The di-aldehyde end-capped oligophenyleneethynylene is of the structure:

where n is 0 to 4 and R is independently H, $C_1$-$C_3$ alkyl, or $C_1$-$C_3$ alkoxy where any of the carbons may be unsubstituted or substituted with: an amine or protected amine comprising substituent; a OH or protected hydroxy comprising substituent; a SH or protected thiol comprising substituent; an amide comprising substituent; or a guanidine or protected guanidine comprising substituent; where the substituent optionally comprises: an $C_2$-$C_5$ alkylene oxide dimer, trimer, tetramer, or pentamer; an unprotected or protected $C_2$-$C_5$ alkylene imine dimer, trimer, tetramer, or pentamer; or N-substituted $C_1$-$C_3$ alkyl alkylene imine dimer, trimer, tetramer, or pentamer. The polyamine is a diamine of the structure:

where X is: $(CR_2)_x$ where x is 1-3 and Rs are independently H, $C_1$-$C_6$ alkyl, or phenyl; $(CR_2)_y C_6 H_z R_{4-z} (CR_2)_y$, where y is 0-2, z is 0-4, and R is independently H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4, and where X is optionally interrupted one or more times with a disulphide, ester, acetal, or ketal. The polyamine is a triamine of the structure:

where Y is:
$((CR_2)_x)_3 CR$ where x is independently 1-3 and Rs are independently H, $C_1$-$C_6$ alkyl,
or phenyl; $((CR_2)_y)_3 C_6 H_z R_{3-z}$ where y is 0-2, z is 0-3, and R is H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4 and where Y is optionally interrupted one or more times with a disulphide, ester, acetal, or ketal. The polyamine is a tetraamine of the structure:

where Z is: $((CR_2)_x)_4 C$ where x is independently 1-3 and Rs are independently H, $C_1$-$C_6$ alkyl, or phenyl; $((CR_2)_y)_4 C_6 H_z R_{2-z}$ where y is 0-2, z is 0-2, and R is H, $C_1$-$C_6$ alkyl, aryl, $NHR'_2$, where R' is $C_1$-$C_6$ alkyl; or $(CH_2)[O(CH_2)_2]_n(CH_2)$ where n is 1 to 4 and where Z is optionally interrupted one or more times with a disulphide, ester, acetal, or ketal. The PEMC can be subsequently protonated with an acid to enhance the water solubility of the PEMC.

An embodiment of the invention is directed to a method of intracellular labeling by introducing an aqueous solution of a protonated PEMC to live cells when the oligophenyleneethynylene has at least one side chain with a protonated amine, where upon irradiation the PEMC fluoresces from within the live cells.

DETAILED DISCLOSURE

Figure 1:
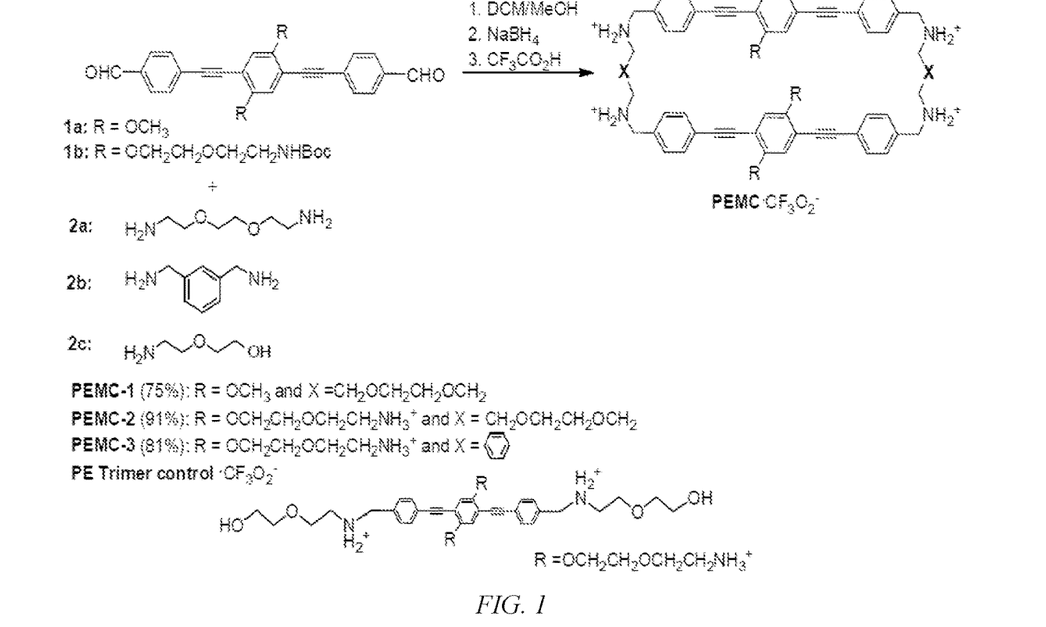
FIG. 1 shows a synthetic scheme of synthesis of phenyleneethynylene macrocycles (PEMCs) according to an embodiment of the invention, and a PE trimer control for comparison.

To combine the advantages of conjugated polymers (CPs) with more chromophores per molecule and conjugated oligomers (COs) with monodispersed molecular weights and fast cellular entry, embodiments of the invention are directed to macrocyclics. The macrocyclics are prepared, according to an embodiment of the invention, using imine-coupling between aldehyde end-capped phenyleneethynylene (PE) trimer units and flexible diamines, as shown in FIG. 1. Alternatively, for polycyclic macrocycles, the amine can be triamines or tetraamines. Because the equilibrium in the imine bond formation can be quantitatively shifted to thermodynamically favoured products, the target macrocycles can be obtained in high yields without accompanying byproducts, where the exemplary PE trimer-based rigid-flexible [2+2] macrocycle (PEMC) is useful for nucleic acids labelling in live cells, according to an embodiment of the invention.

Figure 2A:
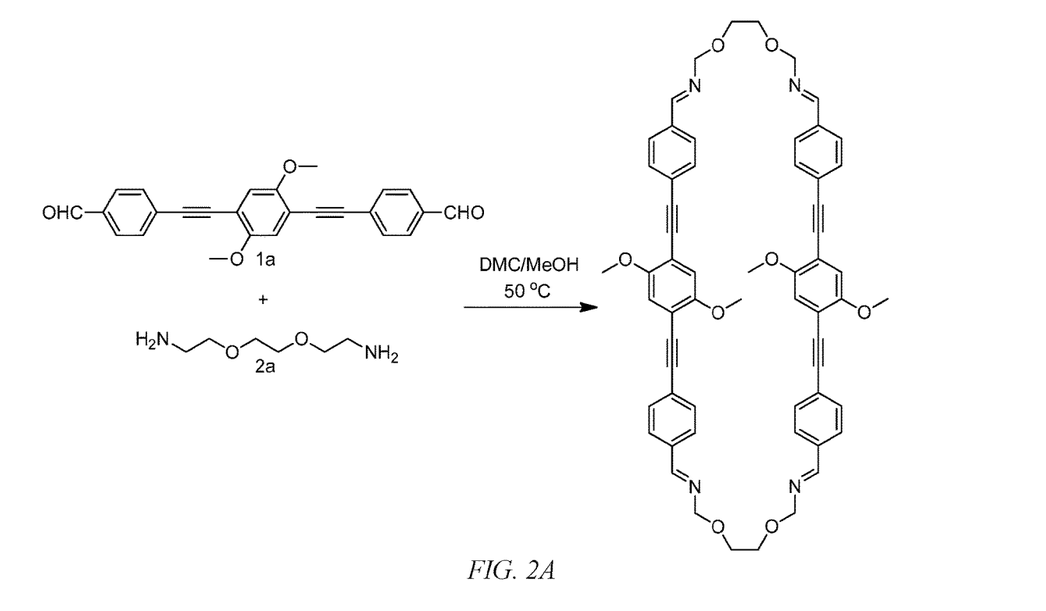
FIG. 2A shows a reaction scheme for the formation of the macrocycle upon condensation of the amines and anhydrides to imines, according to an embodiment of the invention.

Aldehyde-end-capped rigid dimethoxy PE trimers were coupled with flexible amphiphilic diamines to form dimeric macrocycles in high yields, as shown in FIG. 2A. The presence of primary amines at the end of side chains of the PEMC, according to an embodiment of the invention, is advantageous to nucleic acid staining. The PEMCs are approximately three times brighter than the corresponding trimer control and exhibit fast cellular entry, RNA selectivity, and nontoxicity, supporting that cyclization of COs can be a promising technique for improving intracellular targeted labelling.

Figure 2B:
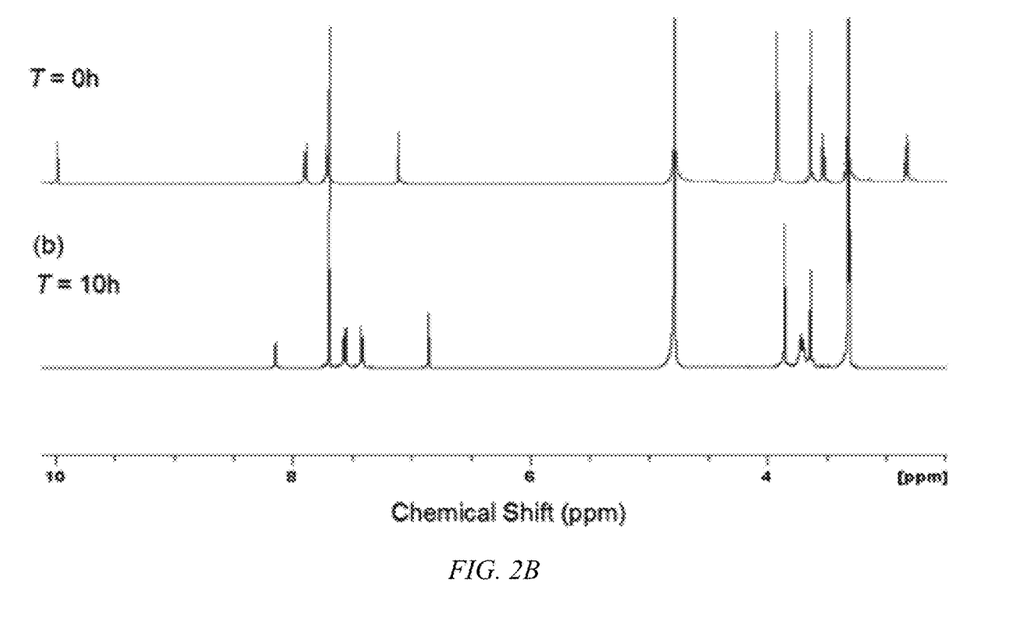
FIG. 2B shows $^1$H NMR spectra of the reaction mixture of FIG. 2A at time zero and after 10 hours, showing the complete reaction of the anhydride to the imine.
Figure 3A:
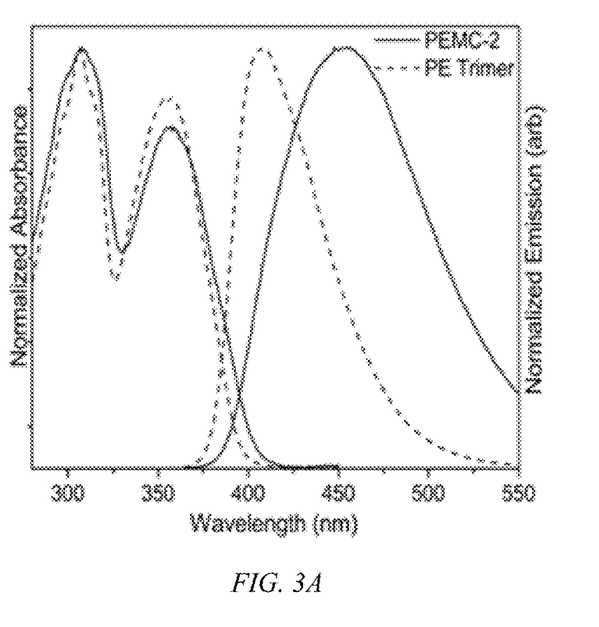
FIG. 3A shows composite absorption and emission spectra for aqueous solutions of PEMC-2, according to an embodiment of the invention, and of a PE trimer control.
Figure 3B:
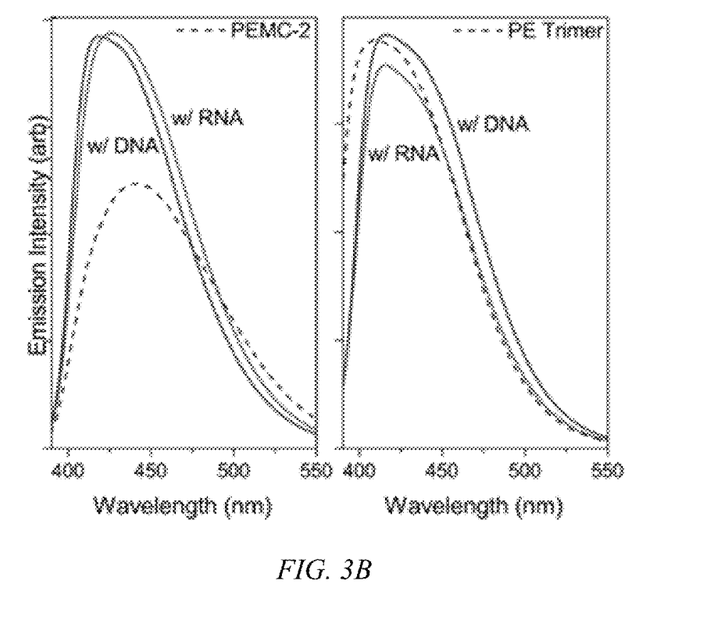
FIG. 3B shows composite emission spectra for aqueous solutions of PEMC-2, according to an embodiment of the invention, and of a PE trimer control in the presence of nucleic acids (NAs).

PEMCs are formed in high yield via imine-bond formation, as can be monitored by proton nuclear magnetic resonance ($^1$H NMR) spectroscopy which shows loss of the aldehyde proton peak at 9.9 ppm and the appearance of an imine proton peak at 8.2 ppm and other proton peaks corresponding chemical shifts without any signals indicating the formation of by-products, as shown in FIG. 2B. As imines generally form in the E-configuration, $H_2N(CR_2)_xNH_2$ does not include ethylenediamine or other connecting groups do not permit the near parallel orientation of the PE trimers, as a conformation that allows formation of the cyclic dimer PEMC is not possible. The PE trimer control was also synthesized by reacting the PE trimer 1b with 2-aminoethoxyethanol followed by reduction of the imine. After reduction of the imine, PEMC-2 exhibits a red shifted absorption and broader emission profiles relative to the PE control, indicating that the two PE trimers in PEMC-2 form an excited state dimer, an excimer, as indicated in FIGS. 3A and 3B, respectively. The QY of PEMC-2 was ~3-fold higher than the corresponding PE trimer, despite having doubled the amounts of amine groups that generally lower QYs.

Figure 4:
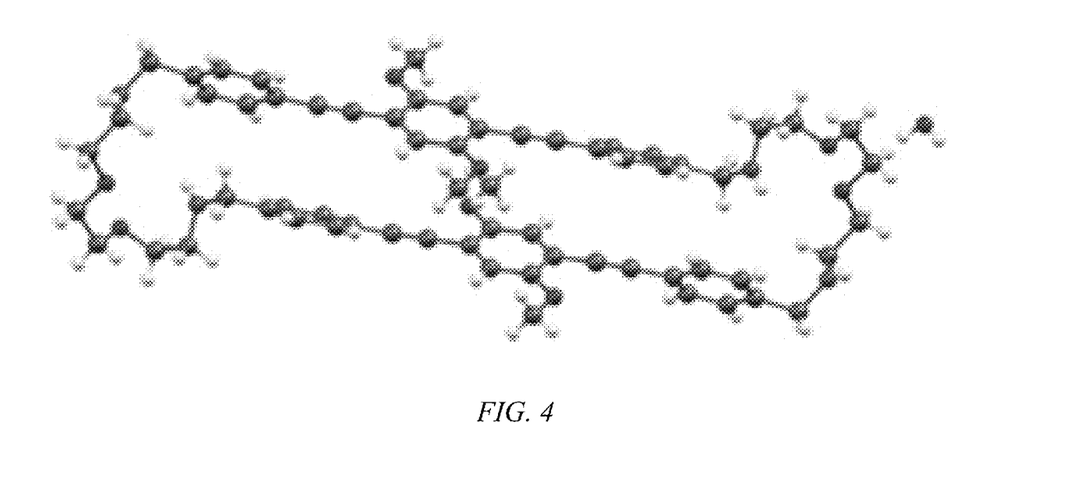
FIG. 4 shows an x-ray structure of PEMC-1, according to an embodiment of the invention.

Plate-shaped crystals of PEMC-1 were obtained from acetonitrile and the solid-state structure was determined by single-crystal X-ray crystallography, as shown in FIG. 4. PEMC-1 crystallizes in the P21/c space group, with one molecule in the unit cell. The crystal structure reveals the two PE units are not in close π-π stacking except for the centre phenyl group. The flexible side chains have an oppositely oriented geometry resembling the aza crown ether structure, resulting in distortion of the end phenyl groups in the trimer and the PE backbone.

In order to gain insight on the structure in an aqueous environment, quantum chemical calculations for geometry optimization and excitation energies of protonated PE control and PEMC-2 were conducted using the density-functional tight-binding (DFTB) method and molecular dynamics calculations. In both PE-trimer and PEMC-2, the formation of intramolecular NH—O hydrogen bonding was observed in the linker moiety. In the case of fully protonated PEMC-2, there is a tendency for sidechains to avoid unfavourable Coulombic repulsion of the positive charges by "wrapping" around the central PE-trimer moiety. Using these structures, we performed time-dependent DFTB calculations using the DFTB+ code and computed excitation energies and oscillator strengths for the 30 lowest singlet excited states (ESI). In the case of the PE-trimer, the HOMO-LUMO excitation occurs at 2.637 eV (=470 nm), whereas the corresponding transition occurs in the PEMC-2 macrocycle at 2.403 eV (=516 nm). The redshift due to excimer formation is 46 nm, which is in good agreement with the experimental emission redshift 50 nm, as shown in FIG. 3a, appears to be due to a π-stacked structure for the ESI.

Trifluoroacetate salted PEMCs are highly soluble in water and exhibit no noticeable cell viability inhibition (ESI). Using human cervical carcinoma cells (HeLa), the metabolic activity of HeLa cells in the presence of macrocycles was monitored; with no viability inhibition was observed for concentrations up to 40 μM, which is considerably lower toxicity than many reported NA selective fluorescent molecules. Cellular entry under the non-energy dependent conditions implies diffusion of macrocycles through the membranes. The entry efficiency of PEMCs and PE controls, as determined by confocal microscopic images, is not decreased under both ATP depletion and 4° C. condition (ESI).

Figure 5A:
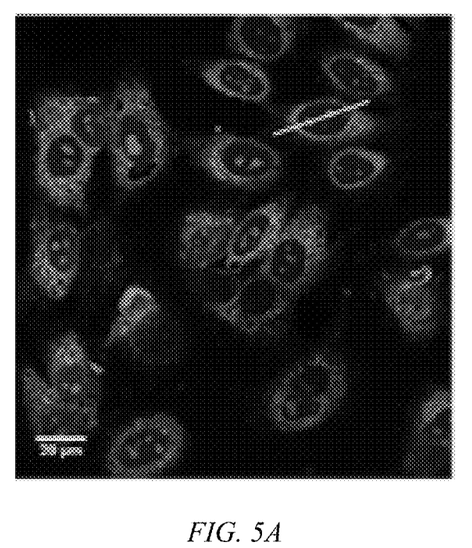
FIG. 5A shows a confocal microscopic image of HeLa cells incubated with PEMC-2, according to an embodiment of the invention, where the image displays PEMC-2 localized in the cytosol and nucleoli.
Figure 5B:
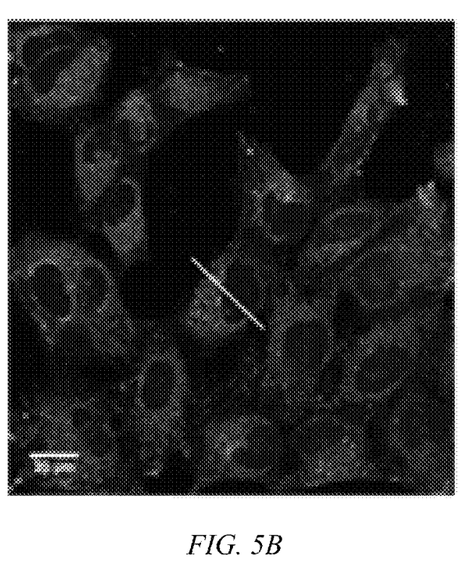
FIG. 5B shows a confocal microscopic image of HeLa cells incubated with PEMC-1, according to an embodiment of the invention, where the image displays PEMC-1 localized in the cytosol.
Figure 5C:
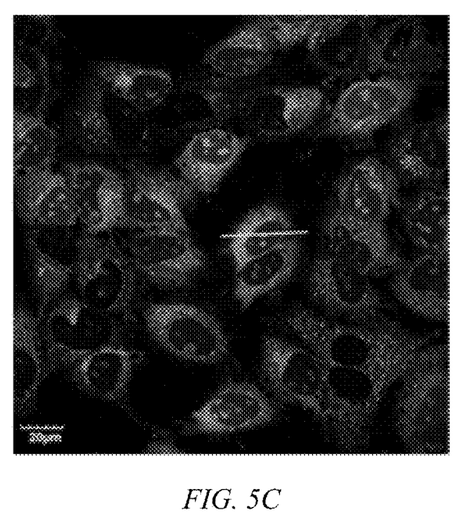
FIG. 5C shows a confocal microscopic image of HeLa cells incubated with PEMC-3, according to an embodiment of the invention, where the image displays PEMC-3 localized in the cytosol and nucleoli.
Figure 5D:
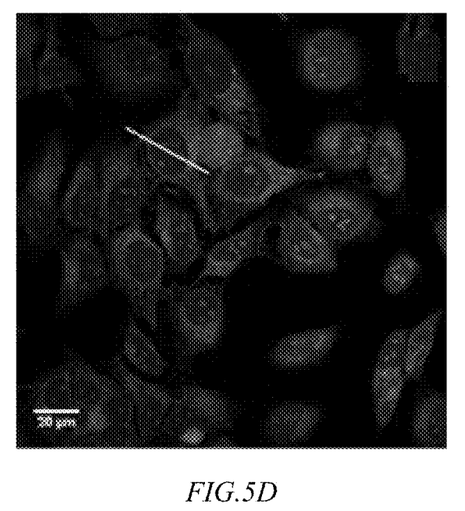
FIG. 5D shows a confocal microscopic image of HeLa cells incubated with PE trimer control where the image displays PE trimer control localized in the cytosol and nucleoli.
Figure 5E:
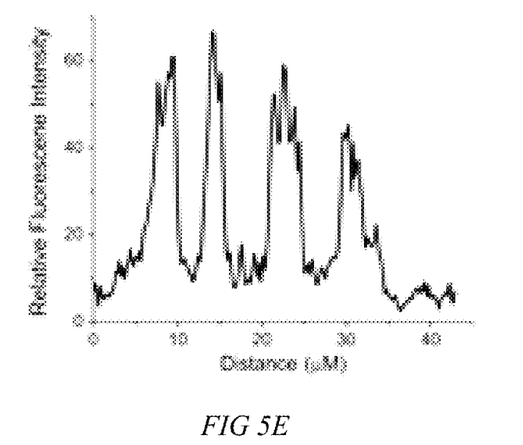
FIG. 5E shows a plot of the fluorescent intensity along the line drawn of the confocal image of FIG. 5A.

As shown in FIG. 5A, PEMC-2, containing primary amine side chains, is localized in the nucleoli along with staining of the cytosol components. In contrast, PEMC-1, as shown in FIG. 5B, without amine side chains, shows staining of the cytosol but not in the nucleus, indicating the primary amine side chains play an important role in penetration of the nuclear membranes and localization in the nucleoli. The relative fluorescent intensity profile along the yellow line in confocal images of FIGS. 5A, 5C, and 5D clearly indicates high localization of PEMC-2, PEMC-3, and PE trimer control in the nucleoli that are the site for ribosomal RNA transcription and processing, as indicated in FIG. 5E, whereas PEMC-1 lacking the amine side chain does not penetrate the membrane. Although structurally similar DNA is abundant in the nucleus, the bright nucleoli spots observed inside of the nucleus with the exposure to PEMC-2 indicate better selectivity to RNA over DNA. When competing double stranded DNA and other proteins co-exist, selective binding of small molecules to single stranded RNA is not common, RNA selectivity is driven by the high electronegative potential surface of the major groove of RNA, which is rich in tandem GC base pairs offering multiple hydrogen bonding sites. The flexible four amine side chains wrapped in the PE trimer units of PEMC-2 appears to promote enhance binding to the RNA.

Figure 6A:
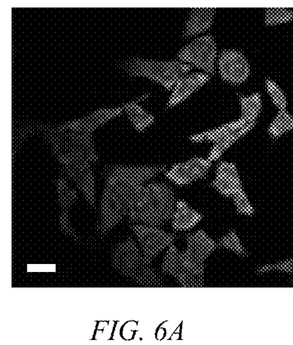
FIG. 6A shows a confocal microscopic image of Hela cells treated with PEMC-2, according to an embodiment of the invention.
Figure 6B:
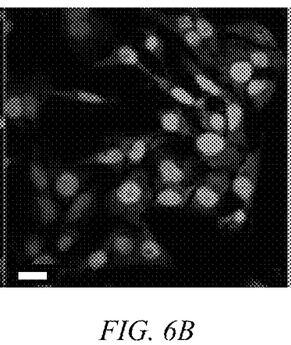
FIG. 6B shows a confocal microscopic image of Hela cells after RNAase treatment and treatment with PEMC-2, according to an embodiment of the invention.
Figure 6C:
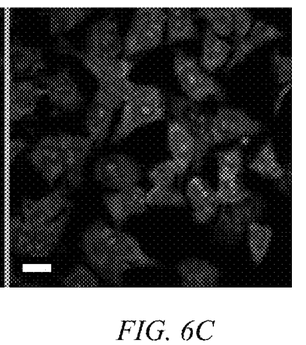
FIG. 6C shows a confocal microscopic image of Hela cells after DNAase treatment and treatment with PEMC-2, according to an embodiment of the invention.
Figure 6D:
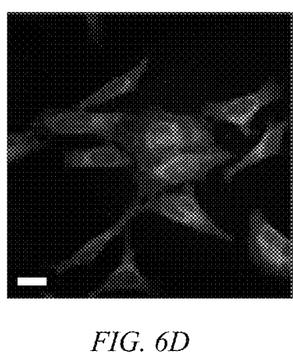
FIG. 6D shows a confocal microscopic image of Hela cells treated with PEMC-1, according to an embodiment of the invention.
Figure 6E:
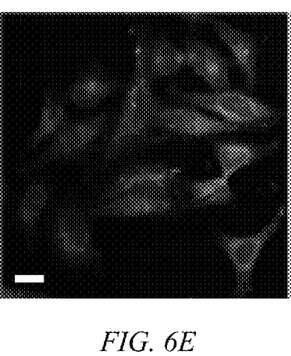
FIG. 6E shows a confocal microscopic image of Hela cells after RNAase treatment and treatment with PEMC-1, according to an embodiment of the invention.
Figure 6F:
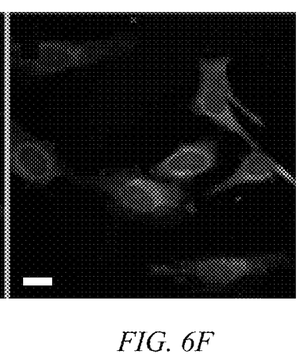
FIG. 6F shows a confocal microscopic image of Hela cells after DNAase treatment and treatment with PEMC-1, according to an embodiment of the invention.
Figure 6G:
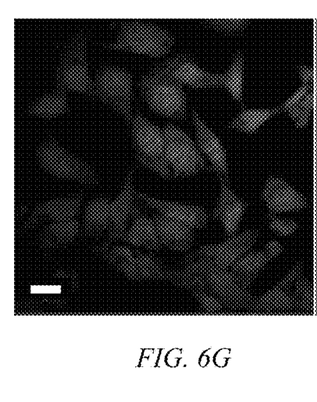
FIG. 6G shows a confocal microscopic image of Hela cells treated with PE trimer control.
Figure 6H:
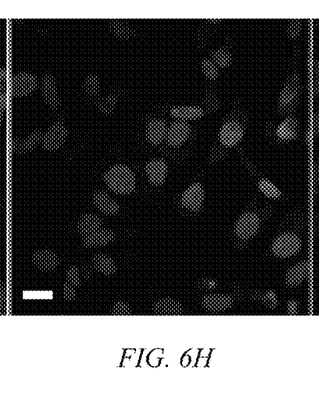
FIG. 6H shows a confocal microscopic image of Hela cells after RNAase treatment and treatment with PE trimer control.
Figure 6I:
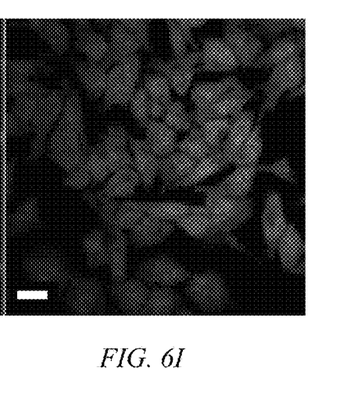
FIG. 6I shows a confocal microscopic image of Hela cells after DNAase treatment and treatment with PE trimer control.

Permeablized HeLa cells incubated with the PEMCs were treated with ribonuclease (RNase) and deoxyribonuclease (DNase). Confocal microscopic images, as shown in FIGS. 6A-6C, using PEMC-2 clearly show nucleus staining before, as shown in FIG. 6A, and after digesting RNA, as shown in FIG. 6B, and, very similarly, after digesting DNA, as shown in FIG. 6C. The imaging patterns using PEMC-1, with no primary amine side chains, display images that have no difference before and after RNase and DNase digestion, as indicated in FIGS. 6D-6F, with PEMC-1 localization in the intracellular compartments without involving NA staining. In order to check whether PEMC-2 exhibits higher fluorescence intensity upon interacting with RNA, the fluorescent intensity of the macrocycle was examined as the amounts of RNA increased, as shown in FIG. 3B. The fluorescent intensity of PEMC-2 slightly increased upon mixing with the excess amounts of nucleic acids (NAs), but no intensity differences between RNA and DNA were observed from the macrocycle. The increased emission intensity, blue-shifted emission maximum, and decreased spectral width of PEMC-2/NA imply the slightly reduced $\pi$-$\pi$ stacking between the two PE trimers in PEMC-2 upon interacting with NAs. The PE trimer control exhibits very small changes in emission upon NA complexation. From the observations, PEMC-2 displays higher affinity to RNA over DNA. The distinguishable nucleus staining after RNase treatment indicates that relatively small amounts of PEMC-2 were also bound to DNA and the fluorescent signals became visible once the intense signals from RNA-bound PEMC-2 were removed by digestion of RNA. The PE trimer control, sharing the same primary amine-containing side chains exhibits a somewhat similar imaging pattern to that of PEMC-2, as shown in FIGS. 5G-5I. However, the overall fluorescent intensity and the contrast between nucleus and nucleolus is much lower, implying that cyclization of PE trimers to a macrocycle can enhance the brightness and RNA selectivity of PEMCs.

In embodiments of the invention, the PE oligomer is not limited to the trimer. The rigid PE oligomer can be a dimer, trimer tetramer, or pentamer, where side chains with functional groups, such as methoxy groups, or any which permit solubilisation in water. Functional groups that can be substituted on the aromatics of the PE oligomers include amines, amides, alcohols and thiols. The aldehyde end-capped PE oligomer has the structure:

where n is 0 to 4, is independently H, $C_1$-$C_3$ alkyl or alkoxy where any of the carbons may be unsubstituted or substituted with: an amine or protected amine comprising substituent; a OH or protected hydroxy comprising substituent; a SH or protected thiol comprising substituent; an amide comprising substituent; or a guanidine or protected guanidine comprising substituent; wherein the substituent can include: an $C_2$-$C_5$ alkylene oxide dimer, trimer, tetramer, or pentamer; an unprotected or protected $C_2$-$C_5$ alkylene imine dimer, trimer, tetramer, or pentamer; or N-substituted $C_1$-$C_3$ alkyl alkylene imine dimer, trimer, tetramer, or pentamer.

In embodiments of the invention, the diamines useful for macrocyclization include: $H_2NCH_2(CR_2)_xCH_2NH_2$ where Rs are independently H, $C_1$-$C_6$ alkyl, or phenyl and x is 1-2; a dialkyl amine substituted aromatic, $H_2NCH_2(CR_2)_yC_6H_zR_{4-z}(CR_2)_y CH_2NH_2$, where y is 0-2, z is 0-4, and R is H, $C_1$-$C_6$ alkyl, aryl, $NHR'_2$, OH; or $H_2N(CH_2)_2[O(CH_2)_2]_nNH_2$, where R' is $C_1$-$C_6$ alkyl, and any of these diamines can be interrupted within the connecting bonds one or more times with a disulphide, ester, acetal, ketal, or any readily cleavable functionality.

In embodiments of the invention, the triamines useful for macrocyclization include: $(H_2NCH_2(CR_2)_x)_3CR$ where x is independently 0-2 and Rs are independently H, $C_1$-$C_6$ alkyl, or phenyl; $(H_2NCH_2(CR_2)_y)_3C_6H_zR_{3-z}$ where y is 0-2, z is 0-3, and R is H, $C_1$-$C_6$ alkyl, aryl, $NHR'_2$, where R' is $C_1$-$C_6$ alkyl; or $(CH_2)_2[O(CH_2)_2]_n(CH_2)_2NH_2$ where n is 1 to 4 and any of these triamines can be interrupted within the connecting bonds one or more times with a disulphide, ester, acetal, ketal, or any readily cleavable functionality.

In embodiments of the invention, the tetraamines useful for macrocyclization include: aliphatic triamine, $(H_2NCH_2(CR_2)_x)_4CR$ where x is independently 0-2 and Rs are independently H, $C_1$-$C_6$ alkyl, or phenyl; $(H_2NCH_2(CR_2)_y)_4C_6H_zR_{2-z}$ where y is 0-2, z is 0-2, and R is H, $C_1$-$C_6$ alkyl, aryl, $NHR'_2$, where R' is $C_1$-$C_6$ alkyl; or $(CH_2)_2[O(CH_2)_2]_n(CH_2)_2NH_2$ where n is 1 to 4 and any of these tetraamines can be interrupted within the connecting bonds one or more times with a disulphide, ester, acetal, ketal, or any readily cleavable functionality.

Figure 7:
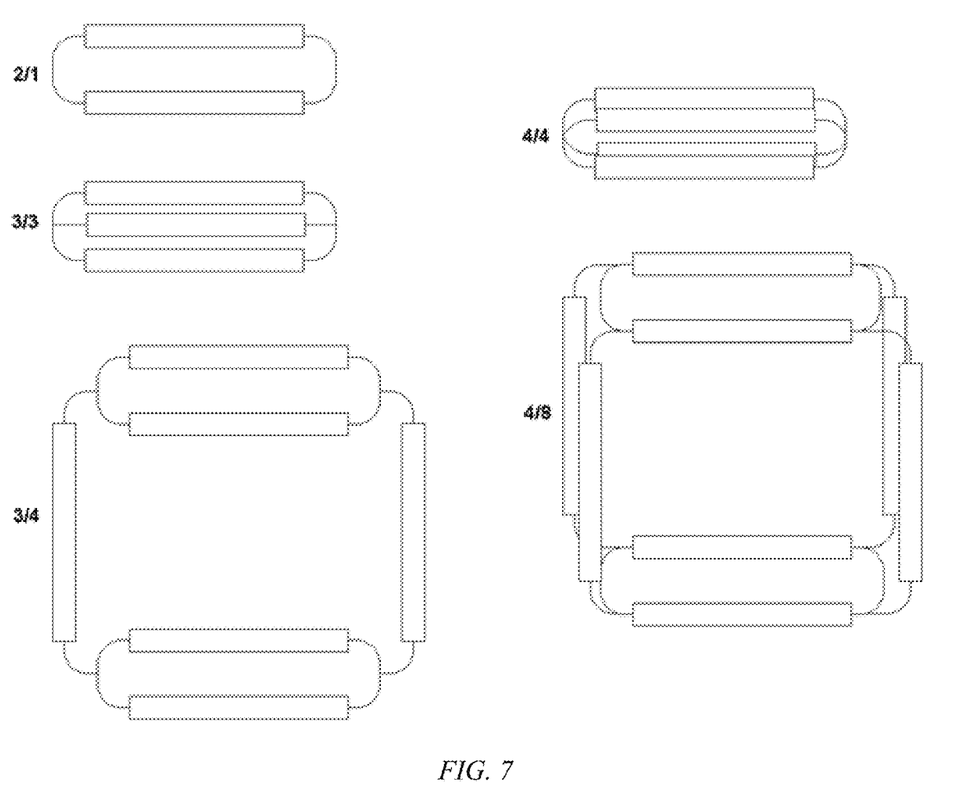
FIG. 7 shows the type of oligomeric macrocycles that can be formed between PE dianhydrides and diamines, triamines, or tetraamines, according to embodiments of the invention.
Figure 8:
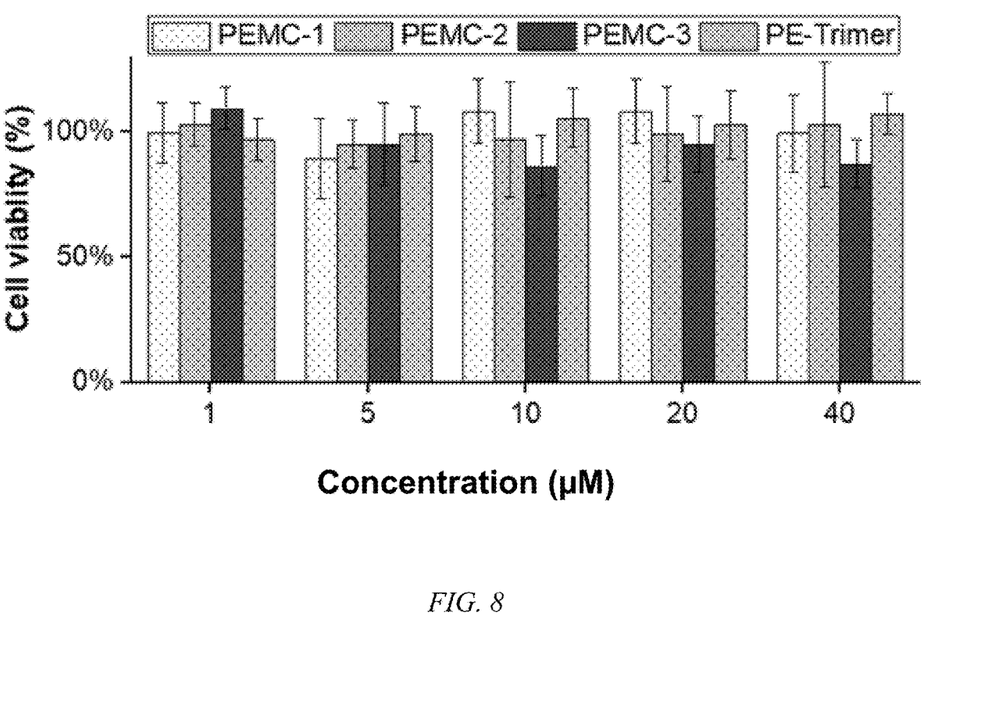
FIG. 8 is a bar chart of HeLa cell viability inhibition of PEMC-1, PEMC-2, and PEMC-3, according to an embodiment of the invention, and PE trimer control.

Synthesis of the PEMCs occurs with incorporation of dimeric connectivities, with little trimer and higher oligomers formed, suggesting that the effective dilution is sufficiently great that the very small equilibrium linear content in the equilibrium mixture is very small oligomers. In this manner, oligomeric macrocyclics contain one or a combination of a plurality of macrocyclics where two repeating unit macrocyclics portions dominate the structure. The number of these portions that are formed depend on the functionality of the amines in the linking repeating units In embodiments of the invention, the amines use for the formation of PEMCs can be: diamine to form a dimer unimacrocycle (2/1); a triamine to form a trimer trimacrocycle (3/3); a triamine to form a hexamer tetramacrocycle (3/4); a tetraamine to form a tetramer tetramacrocycle (4/4); or a tetraamine to form a octamer hexamacrocycle (4/6), whose gross structure is illustrated in FIG. 7 where rectangles represent the PE oligomers and lines represent the links between amine sites connected to the PE oligomers. The hydrodynamic volume of the unimacrocycle, trimacrocycle, tetramacrocycle, and hexamacrocycle are similar when the anhydride end-capped PE is of equal lengths and the distance between the amines of the diamines, triamines, or tetraamines are approximately equal.

Methods and Materials

Chemicals, including solvents, were purchased from Fisher Scientific and used as received. Deuterated solvents were purchased from Cambridge Isotope Laboratories (Cambridge, Mass.). All chemicals and solvents were purchased and used without further purification. Nuclear mag- netic resonance (NMR) spectra were recorded on a 400 MHz Avance Bruker NMR spectrometer. $^1$H and $^{13}$C NMR chemical shifts are given in ppm relative to Si(CH$_3$)$_4$. The mass spectrometric data were conducted on a Bruker Solarix FT-ICRMS. Data for crystal structure was obtained on a Bruker D8 Quest CMOS diffractometer. The crystal was kept at T=296(2) K during data collection. Using APEX3, the structure was solved with the ShelXT 2014/5 structure solution program, using the intrinsic phasing method. The model was refined with version 2016/6 of ShelXL using full matrix least squares on F$^2$ minimization, using the Olex2 GUI. Analytical thin layer chromatography (TLC) was performed on TLC Silica gel 60 F254. The TLC plates were visualized by shortwave (254 nm) or longwave (360 nm) UV light. Flash chromatography on silica gel (230-400 mesh) was performed. UV-vis spectra were recorded on a Varian Cary 50 Bio spectrophotometer. Fluorescence spectra were obtained using a FluoroLog-3 Spectrofluorometer (Jobin Yvon/Horiba). 9,10-diphenylanthracene (QY=1.0) in cyclohexane was used as a fluorescence standard for QY determination. Fourier transform infrared (FTIR) spectra were recorded on a PerkinElmer Spectrum 100 FTIR Spectrometer. Fine polymer powders were directly mounted on an attenuated total reflection (ATR) cell of the spectrometer.

Synthesis of Monomers

4-Ethynylbenzaldehyde

The reaction mixture stirred at room temperature for 3 h under nitrogen atmosphere. On completion, the organic solvent was evaporated to dryness. The residue was redissolved in dichloromethane and filtered through a silica gel column using mixture of ethyl acetate and hexane (1:9) to give compound 5 as brown solid. Yield: 3.7 g (68%). The compound 5 (3.7, 18.288 mmol) was dissolved in a mixture of tetrahydrofuran and methanol (50 mL, 1:1) and anhydrous potassium carbonate (2.5 g, 18.288 mmol) was added. The reaction mixture was allowed to stir at room temperature for 15 min, filtered and washed thoroughly with dichloromethane. The combine filtrate was evaporated and purified through column chromatography using mixture using mixture of ethyl acetate and hexane (2:8) to give compound 6 as yellow solid. Yield: 2.3 g (97%). $^1$H NMR (400 MHz, CDCl$_3$): δ 10.02 (s, 2H), 7.84 (d, J=8.4 Hz, 2H), 7.63 (d, J=8.4 Hz, 2H), 3.29 (s, 1H); $^{13}$C NMR (100 MHz, CDCl$_3$): δ 191.4, 136.1, 132.8, 129.6, 128.4, 82.8, 81.2.

4,4'-((2,5-Dimethoxy-1,4-phenylene)bis(ethyne-2,1-diyl))dibenzaldehyde

Synthesis of 4-ethynylbenzaldehyde (6) was conducted by following the literature procedure.[4] A solution of 4-bromobenzaldehyde (3) (5.0 g, 27.024 mmol) in dry toluene (70 mL) and triethylamine (35 mL) was degassed with nitrogen for 20 min. To this, trimethylsilyl acetylene (4) (2.8 g, 28.507 mmol) was added and the resulting mixture was degassed for additional 15 min. Pd [PPh$_3$]$_4$ (947.2 mg, 1.351 mmol) and CuI (257.4 mg, 1.351 mmol) were added.

Synthesis of monomer 4,4'-((2,5-dimethoxy-1,4-phenylene)bis(ethyne-2,1-diyl))dibenzaldehyde (1a) was conducted by following a literature procedure. Yield: 640 mg (63%). $^1$H NMR (400 MHz, CDCl$_3$): δ 10.03 (s, 2H), 7.88 (d, J=8.0 Hz, 4H), 7.71 (d, J=8.4 Hz, 4H), 7.06 (s, 2H), 3.93 (s, 6H); $^{13}$C NMR (100 MHz, CDCl$_3$): δ 191.5, 154.3, 135.7, 132.4, 129.7, 129.6, 115.9, 113.6, 94.6, 89.8, 56.7.

Di-tert-butyl(((((2,5-diiodo-1,4-phenylene)bis(oxy))bis(ethane-2,1-diyl))bis(oxy))bis ethane-2,1-diyl))dicarbamate

8

1b

Synthesis of di-tert-butyl (((((2,5-diiodo-1,4-phenylene)bis(oxy))bis(ethane-2,1-diyl)) bis(oxy))bis(ethane-2,1-diyl))dicarbamate (8) was according to a literature procedure.

Di-tert-butyl(((((2,5-bis((4-formylphenyl)ethynyl)-1,4-phenylene)bis(oxy))bis(ethane-2,1-diyl))bis(oxy))bis(ethane-2,1-diyl))dicarbamate A solution of compounds 8 (1 g, 1.362 mmol) and 6 (390.0 mg, 2.997 mmol) in a mixed solution of dry tetrahydrofuran and triethylamine (28 mL, 3:1) was degassed with nitrogen for 20 min. Pd(PPh$_3$)$_4$ (47.7 mg, 0.068 mmol) and CuI (13.0 mg, 0.068 mmol) were added. The reaction mixture stirred at 80° C. for 16 h under nitrogen atmosphere. The mixture was allowed to cool down, filtered and the solvent was evaporated. The residue was purified by column chromatography using mixture of ethyl acetate and hexane (4:6) to give di-tert-butyl(((((2,5-bis((4-formylphenyl)ethynyl)-1,4-phenylene)bis(oxy))bis(ethane-2,1-diyl))bis(oxy))bis(ethane-2,1-diyl))dicarbamate monomer 1b as yellow solid. Yield: 480 mg (48%). $^1$H NMR (400 MHz, CDCl$_3$): δ 10.03 (s, 2H), 7.88 (d, J=8.4 Hz, 4H), 7.67 (d, J=8.4 Hz, 4H), 7.09 (s, 2H), 4.92 (br, 2H), 4.22 (t, J=4.8 Hz, 4H), 3.90 (t, J=4.8 Hz, 4H), 3.68 (t, J=5.2 Hz, 4H), 3.34-3.32 (m, 4H), 1.40 (s, 18H); $^{13}$C NMR (100 MHz, CDCl$_3$): δ 191.5, 156.1, 153.9, 135.7, 132.2, 129.8, 129.5, 117.7, 114.4, 94.7, 89.6, 79.4, 70.8, 69.6, 40.6, 28.5. HR-ESI-FT-ICR-MS: m/z calculated for C$_{42}$H$_{48}$N$_2$O$_{10}$ (M+H)$^+$: 741.33817, found: 741.33812.

Synthesis of PEMCs

General Procedure for Macrocycle Synthesis

To an oven dried round bottom flask, 1a or 1b (0.127 mmol) was dissolved in dichloromethane. To this solution, diamines (0.127 mmol) were added and the mixture was diluted with methanol. The reaction mixture was stirred at 50° C. for 10 h and allowed to cool down to room temperature. To the resulting reaction mixture, a solution of sodium borohydride (1.270 mmol) in methanol (5 mL) was added dropwise at 20° C. The reaction mixture was stirred at room temperature for 1 h and then excess sodium borohydride was quenched by adding saturated aqueous sodium bicarbonate solution (1 mL). The solvent was evaporated, and then the residue was re-dissolved in dichloromethane (50 mL). The solution was washed with aqueous ammonium chloride solution (15%), water, and brine. The organic layer was separated, dried over anhydrous sodium sulfate, filtered, and evaporated. The crude macrocycles were purified by column chromatography or recrystallization from acetonitrile.

Prepared from 1a (50.1 mg, 0.127 mmol) and 2a (18.8 mg, 0.127 mmol) in a mixture of dichloromethane (20 mL) and methanol (40 mL) over 10 h by following the general procedure. Recrystallization from acetonitrile yielded PEMC-1 as off-white crystals. Yield: 48.7 mg (75%). $^1$H NMR (400 MHz, CDCl$_3$): δ 7.47 (d, J=8.4 Hz, 8H), 7.27 (d, J=8.4 Hz, 8H), 6.92 (s, 4H), 3.83 (s, 12H), 3.77 (s, 8H), 3.62-3.60 (m, 16H), 3.77 (t, J=4.8 Hz, 8H); $^{13}$C NMR (100 MHz, CDCl$_3$): δ 153.9, 140.8, 131.9, 128.2, 122.0, 115.7, 113.5, 95.1, 85.8, 70.6, 70.5, 56.5, 53.8, 48.9; HR-ESI-FT-ICR-MS: m/z calculated for $C_{64}H_{68}N_4O_8$ (M+H)$^+$: 1021.51099, found: 1021.51117.

PEMC-2 was prepared by reacting 1b (94.1 mg, 0.127 mmol) and 2a (18.8 mg, 0.127 mmol) in a mixed solvent of dichloromethane (40 mL) and methanol (80 mL) over 10 h by following the general procedure. Purification by silica gel column chromatography using a mixture of dichloromethane, methanol, and aq. ammonia as an eluent yielded PEMC-2 as an off-white solid. Yield: 99 mg (91%). $^1$H NMR (400 MHz, CDCl3): δ 7.40 (d, J=8.4 Hz, 8H), 7.26 (d, J=8.4 Hz, 8H), 6.89 (s, 4H), 5.10 (br, 4H), 4.08 (t, J=4.4 Hz, 8H), 3.77-3.75 (m, 16H), 3.63-3.59 (m, 24H), 3.27-3.25 (m, 8H), 2.78 (t, J=4.8 Hz, 8H), 1.39 (s, 36H); $^{13}$C NMR (100 MHz, CDCl3): δ 156.2, 153.6, 140.5, 131.8, 128.4, 122.0, 117.5, 114.3, 95.3, 85.8, 79.2, 70.8, 70.4, 70.3, 69.6, 69.5, 53.6, 48.8, 40.6, 28.6; HR-ESI-FT-ICR-MS: m/z calculated for $C_{96}H_{128}N_8O_{20}$ (M+H)$^+$: 1713.93176, found: 1713.93180.

PEMC-3 was prepared by reacting 1b (94.1 mg, 0.127 mmol) and 2c (68.1 mg, 0.127 mmol) in a mixture of dichloromethane (40 mL) and methanol (80 mL) over 10 h by following the general procedure. Recrystallization from acetonitrile yielded PEMC-3 as off-white solid. Yield: 87 mg (81%). $^1$H NMR (400 MHz, CDCl3): δ 7.47 (d, J=8.0 Hz, 8H), 7.41 (br, 2H), 7.33 (d, J=8.0 Hz, 8H), 7.30 (s, 2H), 7.25 (br, 2H), 6.94 (s, 4H), 5.00 (br, 4H), 4.06 (t, J=4.4 Hz, 8H), 3.84-3.78 (m, 24H), 3.60 (t, J=5.2 Hz, 8H), 3.24-3.23 (m, 8H), 1.38 (s, 36H); $^{13}$C NMR (100 MHz, CDCl3): δ 156.1, 153.7, 153.4, 140.7, 140.1, 131.8, 128.7, 127.7, 127.2, 122.1, 117.6, 114.4, 95.3, 85.7, 79.3, 70.8, 69.6, 52.6, 52.4, 40.6, 28.5. HR-ESI-FT-ICR-MS: m/z calculated for $C_{100}H_{120}N_8O_{16}$ (M+H)$^+$: 1689.88951, found: 1689.88834.

Protonation and Deprotection of Macrocycles

PEMC-1.4TFA

To a solution of PEMC-1 (15 mg, 0.015 mmol) in dichloromethane (1 mL), trifluoroacetic acid (0.5 mL) was added. The reaction mixture was allowed to stir at room temperature for 30 min. The organics were evaporated, and the residue was precipitated from diethylether and dried in vacuo to give compound PEMC-1.4TFA as off-white solid. Yield: 16 mg (100%). $^1$H NMR (400 MHz, MeOD-d$_4$): δ 9.14 (br, 8H), 7.51 (d, J=8.0 Hz, 8H), 7.46 (d, J=8.0 Hz, 8H), 7.00 (s, 4H), 4.18 (s, 8H), 3.80 (s, 12H), 3.70 (t, J=4.8 Hz, 8H), 3.62 (s, 8H), 3.08 (m, 8H).

General Procedure for Boc-Deprotection

To a solution of PEMCs in DMSO (0.5 mL), trifluoroacetic acid (0.1 mL) was added. The mixture was heated at 100° C. in a microwave for 30 min. After cooling, the resulting reaction mixture was dropwise added to diethyl ether and stirred until precipitate was formed. The precipitates were collected and dried in vacuo to give compound PEMCs.8TFA as off-white solid in quantitative yield.

Synthesis of PEMC-2.8TFA Yield: 21 mg (quantitative). $^1$H NMR (400 MHz, MeOD-d$_4$): δ 7.49 (d, J=8.4 Hz, 8H), 7.45 (d, J=8.4 Hz, 8H), 6.94 (s, 4H), 4.24 (s, 8H), 4.16 (t, J=4.0 Hz, 8H), 3.90 (t, J=4.4 Hz, 8H), 3.88-3.79 (m, 16H), 3.71 (s, 8H), 3.26 (t, J=4.8 Hz, 8H), 3.06 (t, J=5.2 Hz, 8H).

Synthesis of PEMC-3.8TFA Yield: 39 mg (99%). $^1$H NMR (400 MHz, D$_2$O): δ 7.60 (m, 6H), 7.40 (d, J=7.6 Hz, 8H), 7.33 (d, J=7.6 Hz, 8H), 7.08 (s, 2H), 7.04 (s, 4H), 4.31-4.39 (m, 16H), 4.14 (s, 8H), 3.97 (br, 8H), 3.86 (t, J=4.8 Hz, 8H), 3.18 (t, J=4.4 Hz, 8H).

Photophysical Properties of PEMCs

TABLE 1

Photophysical properties of PEMCs

| Compounds | Extinction coefficient (ε)(M$^{-1}$cm$^{-1}$) | Quantum Yield (QY)$^a$ (%) |
|---|---|---|
| 1a | 62700 | 31 |
| PEMC-1 | 45200 | 13 |
| PEMC-1•4TFA | 40000 | 3.8 |
| 2a | 57600 | 33 |
| PEMC-2 | 38000 | 12.5 |
| PEMC-2•8TFA | 32400 | 2.4 |
| PEMC-3 | 62500 | 21 |
| PEMC-3•8TFA | 33200 | 2.5 |

$^a$9,10-Diphenylanthracene (QY = 1.0) in cyclohexane was used as a fluorescence standard for QY determination.

Cellular Toxicity Study

HeLa cells were seeded in a 96-well plate were seeded into a 96-well plate (~10,000 cells per well in 200 μL of a complete medium) and allowed to attach for one day at 37° C. under a humidified atmosphere of 5% CO$_2$. A stock solution of PEMC-1, PEMC-2, and PE trimer were added into a complete media and diluted to the required concentrations. Final concentrations of 40 μM, 20 μM, 10 μM, 5 μM, and 1 μM of PEMCs and PE trimer were added into the complete media by dilution with PEMCs and PE-Trimer stock solutions. After additions of PEMCs or PE trimer control, the cells were incubated for additional 18 h. Cells were treated with 10 μL of methylthiazole tetrazolium (MTT) (5 mg/mL in PBS, CALBIOCHEM, Germany) and incubated for 4 h at 37° C. 200 μL of medium was removed gently by using pipette and biological grade DMSO (100 μL) was added to solubilize the purple formazan crystals formed by proliferating cells. Absorbance was measured by a microplate well reader (infinite M1000 PRO, TECAN, Switzerland) at 570 nm. Relative cell viability (%) as a function of PEMCs and PE-Trimer concentration was expressed as percentage relative to the untreated control cells, as shown in FIG. 7. All measurements were performed in triplicate and standard deviation was included in the error bar.

Cell Uptake Studies by Fluorescent Microscopy

HeLa cells were seeded into a 12-well plate (~20,000/well) containing glass coverslips one day before the PEMCs and PE trimer treatment. After incubation in a complete media for 24 h under 5% $CO_2$ at 37° C., the medium was removed and the cells were washed three times with PBS. PEMCs and PE trimer in a fresh complete medium, respectively, was added to cells (final concentration of 10 μM). After 1 h incubation, cells were washed three times with PBS followed by fixation with 4% PFA for 10 min. Fixed cells were then washed three times with PBS and the coverslips were mounted on microscope slides using 1:1 glycerol/PBS mounting medium. Fluorescent images of the cells were obtained using Olympus Fluorview FV1200 confocal microscope (Melville, N.Y. USA) equipped with a bandpass filter for green emission (513-556 nm) and a 60× oil immersion lens (NA 1.35). Image J software (Version 1.50b, U.S. National Institute of Health, Bethesda, Md., USA) was used to process the image.

RNase and DNase Digestion Experiment

In order to confirm the RNA selectivity of PEMCs, DNase and RNase digestion experiments were performed by following a literature procedure. Briefly, cells were fixed by pure methanol for 1 min at room temperature followed by washing with PBS three times. The cell membrane was then permeabilized by adding 1% Triton X-100 for 2 min, and then the cells were washed with PBS three times. Three wells were treated with 10 μM of PEMC-1, next three wells were treated with 10 μM of PEMC-2, and the remaining three wells were treated with 10 μM of PE trimer. Cells were incubated at 37° C. in 5% $CO_2$ for 1 h and washed with PBS three times. To each well of three sets of samples, 100 μL of PBS (as control experiment), 30 μg/ml of DNase (Sigma), and 25 μg/ml DNase-free RNase (GE), respectively, were added and the wells were incubated at 37° C. in 5% $CO_2$ for 2 h. Cells were rinsed by PBS three times before imaging.

Cell Entry Under Non-Energy Dependent Conditions

Cells were pre-treated with 0.05% of sodium azide ($NaN_3$) in the presence of 2-deoxyglucose ($25 \times 10^{-3}$M) for 15 min before PEMC treatment. Cells were incubated with 10 μM of PEMCs and PE trimer, respectively, for 1 h. Cells were washed three times with 1×PBS and fixed with 4% PFA for 10 min. Cells were then washed three times with 1×PBS, and the coverslips were mounted on microscope slides using a 1:1 glycerol/PBS mounting medium. For incubation in 4° C., the medium of cells in a platewell was replaced with pre-cooled medium and PEMC in cooled medium was added to the cells. After incubation in 4° C. for 1 h, cells were washed and fixed for microscopic imaging.

Crystallographic Experimentation

The compound crystallizes in monoclinic P21/c space group, with one half of the molecule in the asymmetric unit. Crystallographic data is provided below in Table 2. The molecule features two intramolecular alkyne pi-phenyl pi interactions, with centroid to bond distances of 3.75-3.85 Å. A solvent water molecule is co-crystallized and forms hydrogen bonds with amine N (N—O distance 2.99 Å) and one of the ether O-atoms (O—O distance 2.92 Å).

TABLE 2

X-ray crystallographic data for PEMC-1.

| | |
|---|---|
| Formula | $C_{64}H_{72}N_4O_{10}$ |
| $D_{calc.}/g\ cm^{-3}$ | 1.234 |
| □/mm$^{-1}$ | 0.083 |
| Formula Weight | 1057.25 |
| Color | colorless |
| Shape | plate |
| Size/mm$^3$ | 0.14 × 0.11 × 0.02 |
| T/K | 296(2) |
| Crystal System | monoclinic |
| Space Group | $P2_1/c$ |
| a/Å | 25.344(2) |
| b/Å | 10.0372(6) |
| c/Å | 11.2060(7) |
| α/° | 90 |
| β/° | 93.783(2) |
| γ/° | 90 |
| V/Å$^3$ | 2844.4(3) |
| Z | 2 |
| Z' | 0.5 |
| Wavelength/Å | 0.710760 |
| Radiation type | MoK$_\alpha$ |
| $\Theta_{min}/°$ | 2.877 |
| $\Theta_{max}/°$ | 25.079 |
| Measured Refl. | 45860 |
| Independent Refl. | 5042 |
| Reflections Used | 1624 |
| $R_{int}$ | 0.4283 |
| Parameters | 354 |
| Restraints | 0 |
| Largest Peak | 0.331 |
| Deepest Hole | −0.228 |
| GooF | 0.997 |
| wR$_2$ (all data) | 0.2005 |
| wR$_2$ | 0.1429 |
| R$_1$ (all data) | 0.3269 |
| R$_1$ | 0.1007 |

Theoretical Simulations

The theoretical structure of the PE-Trimer and PEMC-2 systems were first created using MolView[8] before being optimized in vacuum using the density-functional tight-binding (DFTB) method, including Grimme D3-type dispersion with Becke-Johnson damping (D3-BJ)[9] and the 3ob parameter set. DFTB is an approximate density functional theory (DFT) method based approach utilizing an empirical tight-binding framework and an optimized minimal LCAO Slater-type all-valence basis set in combination with a two-center approximation for Hamiltonian matrix elements. The Coulombic interaction between partial atomic charges was determined using the self-consistent charge (SCC) formalism from third order DFTB (DFTB3), with van der Waals and dispersion interactions being described by Grimme D3-BJ. All vacuum calculations were carried out with the DFTB+ program package version 17.1 with the default convergence criteria for density and geometry optimization procedures. Molecular dynamics calculations were carried to locate global minimum structures were located using DFTB3-D3(BJ) and the Nose-Hoover (NVT) thermostat. The time step and temperature used were 0.4 fs and 298.15 K, respectively, with geometries extracted every 0.52 ps. The final structure was optimized using implicit water with the C-PCM approach as implemented in GAMESS-US.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A phenyleneethynylene macrocycle (PEMC), comprising a cyclic or polycyclic (oligophenyleneethynylene-co-diamine), the oligophenyleneethynylene being a monodispersed dimer, trimer, tetramer, or pentamer, and the diamine comprising the structure:

where X is:
  $(CR_2)_x$ where x is 1-3 and each R is independently H, $C_1$-$C_6$ alkyl, or phenyl;
  $(CR_2)_y C_6 H_z R_{4-z}(CR_2)_y$, where y is 0-2, z is 0-4, and each R is independently H, $C_1$-$C_6$ alkyl, aryl, or $NHR'_2$, where R' is $C_1$-$C_6$ alkyl; or
  $(CH_2)[O(CH_2)_2]_n(CH_2)$ where n is 1 to 4, and
where X is optionally interrupted one or more times with a disulphide group, an ester group, an acetal group, or a ketal group.

2. The PEMC according to claim 1, wherein the oligophenyleneethynylene is of the structure:

where n is 0 to 4 and R is independently H, $C_1$-$C_3$ alkyl, or $C_1$-$C_3$ alkoxy where any of the carbons may be unsubstituted or substituted with: an amine or protected amine comprising a substituent; a OH or protected hydroxy comprising a substituent; a SH or protected thiol comprising a substituent; an amide comprising a substituent; or a guanidine or protected guanidine comprising the substituent; wherein the substituent comprises: an $C_2$-$C_5$ alkylene oxide dimer, trimer, tetramer, or pentamer; an unprotected or protected $C_2$-$C_5$ alkylene imine dimer, trimer, tetramer, or pentamer; or N-substituted $C_1$-$C_3$ alkyl alkylene imine dimer, trimer, tetramer, or pentamer.

3. A PEMC comprising a cyclic or polycyclic (oligophenyleneethynylene-co-triamine), wherein the triamine comprises the structure:

where Y is:
  $((CR_2)_x)_3 CR$ where x is independently 0-3 and each R is independently H, $C_1$-$C_6$ alkyl, or phenyl;
  $((CR_2)_y)_3 C_6 H_z R_{3-z}$ where y is 0-2, z is 0-3, and each R is H, $C_1$-$C_6$ alkyl, aryl, or $NHR'_2$,
  where R' is $C_1$-$C_6$ alkyl; or
  $(CH_2)[O(CH_2)_2]_n(CH_2)$ where n is 1 to 4 and
where Y is optionally interrupted one or more times with a disulphide group, an ester group, an acetal group, or a ketal group.

4. A PEMC comprising a cyclic or polycyclic (oligophenyleneethynylene-co-tetraamine), wherein is the tetraamine comprises the structure:

where Z is:
  $((CR_2)_x)_4 C$ where x is independently 0-3 and each R is independently H, $C_1$-$C_6$ alkyl, or phenyl;
  $((CR_2)_y)_4 C_6 H_z R_{2-z}$ where y is 0-2, z is 0-2, and each R is H, $C_1$-$C_6$ alkyl, aryl, or $NHR'_2$, where R' is $C_1$-$C_6$ alkyl; or
  $(CH_2)[O(CH_2)_2](CH_2)$ where n is 1 to 4 and
where Z is optionally interrupted one or more times with a disulphide group, an ester group, an acetal group, or a ketal group.

5. The PEMC according to claim 1, wherein the cyclic (oligophenyleneethynylene-co-diamine) is a unimacrocycle (2/1).

6. The PEMC according to claim 3, wherein the polycyclic (oligophenyleneethynylene-co-triamine) is a trimacrocycle (3/3) or a tetramacrocycle (3/6).

7. The PEMC according to claim 1, wherein the cyclic (oligophenyleneethynylene-co-diamine) is:

where: X is $CH_2OCH_2CH_2OCH_2$, $C_6H_4$, or $CH_2OCH_2$;
R is $OCH_3$, or $OCH_2CH_2O\ CH_2CH_2NH_2$.

8. The PEMC according to claim 1, wherein the amines of the cyclic (oligophenyleneethynylene-co-diamine) are in the form of an ammonium ion paired with an anion.

9. The PEMC according to claim 8, wherein the anion is a trifluoroacetate, acetate, or a halide.

10. A method of preparing a PEMC according to claim 1, comprising:
  providing a monodispersed di-aldehyde end-capped oligophenyleneethynylene;
  providing a diamine;
  combining the monodispersed di-aldehyde end-capped oligophenyleneethynylene with the diamine to form a macrocyclic imine; and
  reducing the imine to an amine to form a cyclic or polycyclic (oligophenyleneethynylene-co-diamine).

11. The method according to claim 10, wherein the di-aldehyde end-capped oligophenyleneethynylene is of the structure:

where n is 0 to 4 and R is independently H, $C_1$-$C_3$ alkyl, or $C_1$-$C_3$ alkoxy wherein any of the carbons may be unsubstituted or substituted with: an amine or protected amine comprising a substituent; a OH or protected hydroxy comprising a substituent; a SH or protected thiol comprising a substituent; an amide comprising a substituent; or a guanidine or protected guanidine comprising a substituent; wherein the substituent comprises: an $C_2$-$C_5$ alkylene oxide dimer, trimer, tetramer, or pentamer; an unprotected or protected $C_2$-$C_5$ alkylene imine dimer, trimer, tetramer, or pentamer; or N-substituted $C_1$-$C_3$ alkyl alkylene imine dimer, trimer, tetramer, or pentamer.

12. The method according to claim 10, wherein the polyamine is a diamine of the structure:

where X is:
  $(CR_2)_x$ where x is 1-3 and each R is independently H, $C_1$-$C_6$ alkyl, or phenyl;
  $(CR_2)_y C_6 H_z R_{4-z} (CR_2)_y$, where y is 0-2, z is 0-4, and each R is independently H, $C_1$-$C_6$ alkyl, aryl, or $NHR'_2$, where R' is $C_1$-$C_6$ alkyl; or
  $(CH_2)[O(CH_2)_2]_n(CH_2)$ where n is 1 to 4 and
where X is optionally interrupted one or more times with a disulphide group, an ester group, an acetal group, or a ketal group.

13. The method according to claim 10, wherein the reducing comprises combining with $NaBH_4$.

14. The method according to claim 10, further comprising protonating with an acid.

15. The method according to claim 14, wherein the acid is trifluoroacetic acid, acetic acid, or a hydrogen halide.

16. A method of intracellular labeling, comprising providing an aqueous solution of a protonated PEMC according to claim 1 to plurality of live cells, wherein the oligophenyleneethynylene comprises at least one side chain with a protonated amine, where upon irradiation the PEMC fluoresces from within the live cells.

17. The PEMC according to claim 4, wherein the polycyclic oligo (oligophenyleneethynylene-co-tetraamine) is a tetramacrocycle (4/4); or a hexamacrocycle (4/6).

18. A method of preparing a PEMC according to claim 3, comprising:
  providing a monodispersed di-aldehyde end-capped oligophenyleneethynylene;
  providing a triamine;
  combining the monodispersed di-aldehyde end-capped oligophenyleneethynylene with the triamine to form a macrocyclic imine; and
  reducing the imine to an amine to form a cyclic or polycyclic (oligophenyleneethynylene-co-triamine).

19. A method of preparing a PEMC according to claim 4, comprising:
  providing a monodispersed di-aldehyde end-capped oligophenyleneethynylene;
  providing a tetraamine;
  combining the monodispersed di-aldehyde end-capped oligophenyleneethynylene with the tetraamine to form a macrocyclic imine; and
  reducing the imine to an amine to form a cyclic or polycyclic (oligophenyleneethynylene-co-tetraamine).

20. A method of intracellular labeling, comprising providing an aqueous solution of a protonated PEMC according to claim 3 to plurality of live cells, wherein the oligophenyleneethynylene comprises at least one side chain with a protonated amine, wherein upon irradiation the PEMC fluoresces from within the live cells.

* * * * *